United States Patent [19]

Burzynski

[11] Patent Number: 5,391,575
[45] Date of Patent: Feb. 21, 1995

[54] METHOD FOR TREATING NEUROFIBROMATOSIS

[76] Inventor: Stanislaw R. Burzynski, 20 W. Rivercrest, Houston, Tex. 77042

[21] Appl. No.: 237,772

[22] Filed: May 4, 1994

[51] Int. Cl.$^6$ ............................................. A61K 31/195
[52] U.S. Cl. ..................................... 514/563; 514/561; 514/568
[58] Field of Search .......................... 514/561, 563, 568

[56] References Cited

U.S. PATENT DOCUMENTS

| | | | |
|---|---|---|---|
| 4,559,325 | 12/1985 | Burzynski | 514/21 |
| 5,116,622 | 5/1992 | Burzynski | 424/545 |
| 5,227,292 | 7/1993 | White et al. | 435/69.1 |
| 5,244,922 | 9/1993 | Burzynski | 514/561 |

OTHER PUBLICATIONS

The 18th International Congress of Chemotherapy, Stockholm, Sweden (Jun. 27–Jul. 2, 1993).

*Primary Examiner*—Raymond Henley, III
*Assistant Examiner*—T. J. Criares
*Attorney, Agent, or Firm*—Arnold, White & Durkee

[57] ABSTRACT

The present invention provides methods for treating neurofibromatosis in humans by administering to an afflicted host pharmaceutical compositions containing a therapeutically effective amount of a combination of

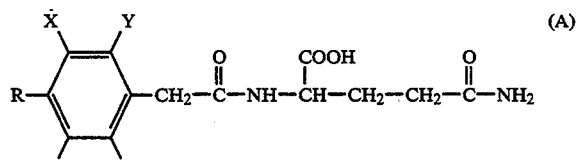

and

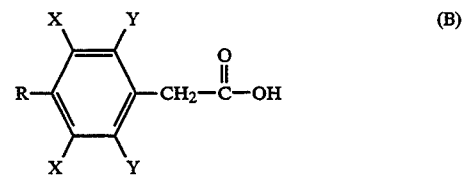

in a weight ratio ranging from about 1:1 to about 1:10 (A:B);
wherein R is OH, NH$_2$, OW, or H;
X is H, F, Cl, Br, I, OH, OW, NO$_2$ or NH$_2$;
Y is H, F, Cl, Br, or I;
W is

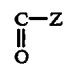

or a C$_1$ to C$_2$ aliphatic group;
Z is an aliphatic or aromatic group of C$_1$ to C$_{12}$;
X and Y can both vary within the compound; or pharmaceutically acceptable salts thereof.

Particularly disclosed herein is a composition comprising a 1:4 ratio of the sodium salts of phenylacetylglutamine and phenylacetic acid, formulated in both oral and parenteral forms. Typically, the patient is given the combination composition from 1 to 20 g/day in divided doses. After several months of treatment patients exhibit significant decrease in number and size of nodules.

6 Claims, No Drawings

METHOD FOR TREATING NEUROFIBROMATOSIS

FIELD OF THE INVENTION

The present invention relates to the use of phenylacetyl derivatives in the treatment of neurofibromatosis.

BACKGROUND OF THE INVENTION

Neurofibromatosis is an inherited condition, which involves development of changes in the nervous system, skin, bones, and muscles manifested by the presence of multiple soft nodules, neurofibromas and associated with hyperpigmented spots. The disease is inherited as an autosomal dominant trait. German physician, Von Recklinghausen, is given the credit for clinical description of this condition (Von Recklinghausen, F., "Uber die multiplen fibrome der Haut und ihre Beziehung zu den multiplen, "Neuromen.", Hirschwald, Berlin (1882)). However, the evidence exists that the disease has been described earlier. The disease exists in two different forms: Type 1, known as Von Recklinghausen's disease, and Type 2. The gene for Type 1, NF1, has been located on chromosome 17 and for Type 2, NF2, on chromosome 22. It is estimated that one person in 4,000 inherits the trait for Type 1, and one person in 50,000 for Type 2.

Neurofibromatosis Type 1 is characterized by neurofibromas and café-au-lait spots. In addition, the patient may suffer from optic glioma, involvement of the bones and have Lisch nodules in the iris.

In neurofibromatosis Type 2, the patient has acoustic neuromas, meningiomas, and less frequently ependymomas and primitive neuroectodermal tumors located intracranially and intraspinally. A number of other neoplastic conditions occur in these patients, including neuroblastoma, Wilms' tumor, leukemia, pheochromocytoma, and thyroid carcinoma.

The disease is often not inherited in a straight-forward manner, but results from the factors that cause an imbalance in gene expression. This means that it may be transmitted by the nonmendelian process, such as genomic imprinting, whereby the expression or lack of expression of the gene is determined by the parental origin of the gene in a specific situation. Specifically, the differences in the material and paternal genes relate to the degree of methylation (Barlow, D. P., "Methylation and Imprinting: from Host Defense to Gene Regulation," Science 260:309-310 (1993); Ferguson-Smith, A. C., Reik, W., Surani, M. A., "Genomic Imprinting and Cancer," Cancer Surv. 9:487-503 (1990); and Reik, W.,"Genomic Imprinting and Genetic Disorders in Man," Trends Genet. 5:331-336 (1989)). The genes which are hypomethylated are transcriptionally active, whereas hypermethylated are inactive. This differs from the classical concept of inheritance, which assumes that alleles inherited from the paternal and maternal side are equally expressed.

The clinical features of the disorder are startlingly variable, even within the same family, indicating that other events must play a role in the eventual phenotype of the disease. The diagnostic criteria for NF1 include the presence of two or more of the following: (1) six or more café-au-lait macules more than 15 mm in greatest diameter in postpubertal individuals, or 5 mm in prepubertal individuals; (2) two or more neurofibromas of any type, or one plexiform neurofibroma; (3) freckling in the axillary or inguinal regions; (4) optic glioma; (5) two or more Lisch nodules (iris hamartomas); (6) a distinctive bony lesion such as sphenoid dysplasia or thinning of long-bone cortex, with or without pseudoarthrosis; (7) a first degree relative with NF1 (Von Recklinghausen, F., "Uber die multiplen fibrome der Haut und ihre Beziehung zu den multiplen, "Neuromen.", Hirschwald, Berlin (1882)). The penetrance of NF1 is extremely high if individuals are carefully examined, including the use of a slit-lamp to detect Lisch nodules. Under those circumstances, it is rare to identify an adult obligate gene carrier who does not meet the criteria listed above (Barlow, D. P., "Methylation and Imprinting: from Host Defense to Gene Regulation," Science 260:309-310 (1993)).

The diagnosis of neurofibromatosis Type 2 can be established when one of the following is present: (1) bilateral 8th cranial nerve masses, (2) first degree relative with neurofibromatosis Type 2, and either unilateral 8th nerve mass or any one of the following: neurofibroma, meningioma, glioma, schwannoma, posterior capsular cataract or opacity at a young age (Neurofibromatosis: National Institutes of Health: Consensus Development Conference Statement 6:1 (1987)).

Current methods of treatment of neurofibromatosis focus on alleviation of the symptoms. Skin lesions are removed through cosmetic surgery. Intracranial and intraspinal nodules are treated by surgery, irradiation, or chemotherapy.

The nodules located in the central nervous system can cause neurological deficit. Depending on the nodule location, the patient may have facial nerve paralysis, decreased hearing or deafness, decreased visual acuity or visual field defects, the symptoms of increased intracranial pressure, paralysis, and diencephalic syndrome. The involvement of the superior eyelid and the eyeball can cause congenital glaucoma, the changes in the bone can result in scoliosis, kyphosis, pseudoarthrosis and bowing of the tibia. Approximately 40% of patients have learning disabilities and 10% mental retardation. The patient who has significant neurological symptoms can be helped by surgical resection of the nodule. Radiation therapy and cytotoxic chemotherapy have been applied in the attempts to reduce the size of the nodules.

Without wishing to bound to any proposed theory, the present inventor postulates that the human body possesses a Biochemical Defense System (BDS) (Burzynski, S. R., Internat. J. Exp. Clin. Chemother. 2:63 (1989) and Burzynski, S. R., 17th Internat. Cong. Chemother., Berlin (1991)). This system parallels the immune defense, but protects the organism against the enemy within the body. The main purpose is no longer the defense against the micro-organism, but defense against defective cells. Chemical components of this biochemical defense system are peptides, amino acid derivatives and organic acids defined as antineoplastons (Burzynski, S. R., Physiol. Chem. Phys. 8:275 (1976) and Burzynski, S. R., U.S. Pat. No. 4,470,970). The mechanism of defense is based not on destruction, but on the reprogramming of defective cells through induction of differentiation.

Antineoplastons discovered by the inventor are small molecular peptides, amino acid derivatives, and certain organic acids, which protect the organism against the development of cancer by a nonimmune mechanism (Burzynski, S. R., "Antineoplastons: Biochemical Defense Against Cancer," Physiol. Chem. Phys. 8:275-279 (1976) and Burzynski, S. R., "Novel Differentiation Inducers," *Recent Advances in Chemotherapy*, Adam, D. (Ed.), Futuramed Publishers, Munich, Germany (1992)).

The research on antineoplastons began in Poland in 1967 (Burzynski, S. R., *Experientia* 25:490 (1969) and Burzynski, S. R., *Drugs Exptl. Clin. Res. Suppl.* 1 12:1 (1986)). Initially, the work concentrated on the isolation of peptides which exist in the blood of healthy people and are deficient in cancer patients. Due to the small amount of raw material available for the study, in the following years, antineoplastons were isolated from urine instead of blood. In 1980, the structure of the first antineoplaston was identified and reproduced synthetically (Burzynski, S. R. et at., *Proc. 13th Internat. Cong. Chemother.*, Vienna, Austria 17, P.S. 12. 4. 11-4(1983)).

Antineoplastons are divided into two groups. One group contains compounds which have a wide spectrum of activity and includes Antineoplaston A1, A2, A3, A4, A5, A10, AS2-1 and AS2-5. Antineoplastons A1, A2, A3, A4 and A5 contain peptides isolated from urine, and Antineoplaston A10, AS2-1 and AS2-5 are synthetic products. See, e.g., U.S. Pat. Nos. 4,470,970, 4,558,057 and 4,559,325. In addition to the first group, there are antineoplastons that are active against a single specific type of neoplasm, such as Antineoplaston H, L and 0. Antineoplaston A10 is the first active ingredient isolated and reproduced by synthesis. Acid hydrolysis of Antineoplaston A10 initially produces phenylacetylglutamine and phenylacetylisoglutamine. When hydrolysis is carried further, the products of reaction include phenylacetic acid, glutamic acid and ammonia. The sodium salt of phenylacetylglutamine was named Antineoplaston AS2-5 and the mixture of the sodium salts of phenylacetyl/glutamine and phenylacetic acid in the ratio of 1:4 was named Antineoplaston AS2-1 (Burzynski, S. R. et at., *Drugs Exptl. Clin. Res. Suppl.* 1 12:11 (1986)).

The mechanism of action of Antineoplaston A2, A3, A5 and AS2-1 involves inhibition of methylation of DNA. The methylation of DNA is a complex, enzymatic reaction which requires three enzymes: methyltransferase, methionine adenos yltransferase, and S-adenosylhomocysteine hydrolase. Numerous published data confirm that antineoplastons are effective hypomethylating agents (Liau, M. C., Burzynski, S. R., "Altered Methylation Complex Isoenzymes as Selective Targets for Cancer Chemotherapy," *Drugs Exptl. Clin. Res.* 12 (Suppl. 1):77-86 (1986); Liau, M. C., Lee, S. S., Burzynski, S. R., "Modulation of Cancer Methylation Complex Isozymes as a Decisive Factor in the Induction of Terminal Differentiation Mediated by Antineoplaston A5,"*Internat. J. Tissue Reactions* 12 (Suppl.):-27-36 (1990); Lee, S. S., Burzynski, S. R., "Induction of Differentiation of HL-60 Human Promyelocytic Leukemic Cell by Antineoplaston A5," *Internat. J. Tissue Reactions* 12 (Suppl.):37-42 (1990); Liau, M. C., Lee, S. S., Burzynski, S. R., "Differentiation Inducing Components of Antineoplaston A5," *Adv. Exptl. Clin. Chemother.* 6:9-25 (1988); Liau, M. C., Lee, S. S., Burzynski, S. R., "Hypomethylation of Nucleic Acids: A Key to the Induction of Terminal Differentiation," *Internat. J. Exptl. Clin. Chemother.* 2:187-199 (1989); Lee, S. S., Burzynski, S. R., "Inducibility of HL-60 Leukemic Cells to Undergo Terminal Differentiation After Repeated Treatment with Antineoplaston A5, " *Internat. J. Exptl. Clin. Chemother.* 3:125-128 (1990); Lee, S. S., Burzynski, S. R., "Antineoplaston A5: A Growth Inhibitor for Cancerous Cells and Growth Stimulator for Normal Cells," *Internat. J. Exptl. Clin. Chemother.* 4:63-65 (1991); Liau, M. C., Luong, Y., Liau, C. P., Burzynski, S. R., "Prevention of Drug-Induced DNA Hypermethylation by Antineoplastons," *Recent Advances in Chemotherapy*, Adam, D. (Ed.), Futuramed Publishers, Munich, Germany (1992); and Liau, M. C., Liau, C. P., Burzynski, S. R., "Potentiation of Induced Terminal Differentiation by Phenylacetic Acid and Related Chemicals," *Internat. J. Exptl. Clin. Chemother.* 5:9-17 (1992)).

In the case where the inherited disorder, such as NF1 or NF2, is due to inactivity of the gene, which is hypermethylated, decreasing methylation of such gene can result in expression of the gene, and theoretically in alleviation of the signs and symptoms of the disease.

SUMMARY OF THE INVENTION

The present invention provides methods for treating neurofibromatosis in humans by administering to the afflicted patient a pharmaceutical composition containing a pharmaceutically acceptable carrier and a therapeutically effective amount of a combination of

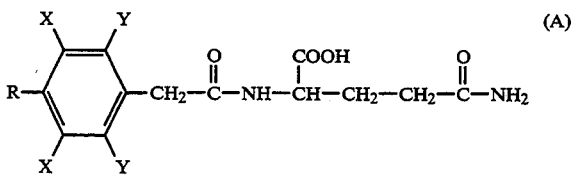

and

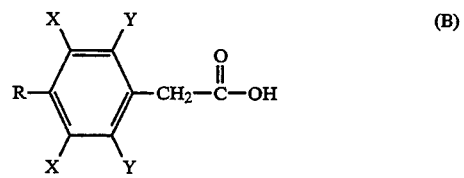

in a weight ratio ranging from about 1:1 to about 1:10 (A: B);

wherein R is OH, NH$_2$, OW, or H;
X is H, F, Cl, Br, I, OH, OW, NO$_2$ or NH$_2$;
Y is H, F, Cl, I or Br;
W is

or a C$_1$ to C$_{12}$ aliphatic group;

Z is an aliphatic or aromatic group of from C$_1$ to C$_{12}$;
X and Y can both vary within the compound; or
pharmaceutically acceptable salts thereof.

As used herein, "pharmaceutically acceptable salts" means salts having the biological activity of the parent compound and lacking unusually toxic activity at the selected administration level. Such salts include, but are not limited to, inorganic sodium, potassium and ammonium salts, organic diethanolamine, cyclohexylamine, and amino acid salts.

The pharmaceutical compositions of the present invention can be administered by using conventional modes of administration, e.g., orally, parenterally, and the like. The pharmaceutical compositions of the present invention comprise a suitable pharmaceutically acceptable carder and the combination of active phenylacetylglutamine and phenylacetate derivatives in an amount effective to ameliorate the symptoms heralding neurofibromatosis, such as for example reducing nodule size and number, and reducing presence of café-au-lait macules and freckling.

In treatments using the pharmaceutical combination, a therapeutically effective dosage regimen should be used. Generally, in the treatment of neurofibromatosis, a proper dosage regimen requires providing the medication over a period of time to achieve noticeable therapeutic effects, such as alleviating the presence of café-au-lait macules, neurofibromatosis, freckling, and reducing nodule size. As used herein, the expression "therapeutically effective amount" or dosage, or regimen means that amount, dosage, or regimen which results in sufficient concentrations of the active ingredient combination at the cellular or tissue site of manifestation effective to prevent, arrest or ameliorate the symptomatic dysfunction, most notably a reduction in nodule size and number.

A particular combination of two compounds, termed herein Antineoplaston AS2-1 (1:4 ratio of sodium salt of phenylacetylglutamine and sodium salt of phenylacetic acid), is particularly preferred and has been administered to human patients for the purpose of treating neurofibromatosis in the form of 500 mg capsules or 80 mg/ml to 100 mg/ml intravenous infusions.

DETAILED DESCRIPTION OF THE PREFERRED EMBODIMENTS

AS2-1 has two known mechanisms of action. The first mechanism is directed at the protein synthesis in the cells and depends on the reduction of the concentration of L-glutamine in the cells and substitution of L-glutamine by phenylacetylglutamine. The second mechanism of action depends on inhibition of methylation of DNA. In case of neurofibromatosis originating from genomic imprinting, the second mechanism may play an important part in the reduction of the signs and symptoms of the disease. If neurofibromatosis results from hypermethylation of neurofibromatosis gene, then decreasing of the methylation of the DNA, of which the gene consists, will allow for expression of the gene.

I. Methods of Preparing the Compounds

Desired R,X,Y substituted derivatives of phenylacetic acid can be purchased commercially or prepared synthetically by methods known to those skilled in the art according to well established rules of electrophilic and nucleophilic aromatic substitution. For example, 4-hydroxyphenylacetic acid, which is commercially available from Aldrich Chemical Company, Inc., can be nitrated with dilute $HNO_3$ to produce 4-hydroxy-3nitrophenylacetic acid that is used as is in the next step of reaction. Alternatively, the nitro group in 4-hydroxy-3-nitrophenylacetic acid can be reduced to the corresponding amine and then reacted with sodium nitrite in acid to form the diazonium salt, that can be converted into a wide range of functional groups, including chloro, fluoro, bromo and hydroxyl. Phenylacetic acid can alternatively be nitrated in the 4-position to produce 4nitrophenylacetic acid, that is used as is in the reaction or convened to the diazonium salt and derivatized. The nitro group can be reduced to the corresponding amino group as a final step of reaction by methods known to those skilled in the art, including catalytic hydrogenation.

The compounds of this invention can be prepared by condensation of the appropriate R,X,Y substituted phenylacetic acid derivative with L-glutamine to produce the corresponding R,X, Y substituted phenylacetylglutamine derivative. The condensation reaction can be facilitated by prior activation of the phenylacetic acid derivative with a reagent such as N-hydroxysuccinimide in the presence of DCC (N,N-dicyclohexylcarbodiimide), 2-mercaptothiazoline in the presence of DCC, or DCC alone. These reactions are described in more detail in Burzynski, *Drugs of the Future* 10(2): 103 (1985).

II. Preparation of Pharmaceutical Compositions and Mode of Administration

As stated above, the combination of R,X,Y substituted phenylacetic acid and R,X,Y substituted phenylacetylglutamine of the present invention is useful in the treatment of neurofibromatosis. Pharmaceutical compositions, including these active compounds, can be prepared as described below.

Mixtures of the active compounds, or pharmaceutically acceptable salts thereof, are included in the pharmaceutically acceptable carrier or diluent in an amount sufficient to exert a therapeutic effect without serious side effect. The combination of active materials can be administered systemically by any appropriate route, for example, orally, parenterally, intravenously, intradermally, subcutaneously, or intraperitoneally, in liquid or solid form.

The concentration of active compounds in the drug composition will depend upon absorption, inactivation, and excretion rates of the active compound as well as other factors known to those skilled in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions.

The combination active ingredient may be administered at once, or may be divided into a number of smaller doses to be administered at varying intervals of time, e.g., 1 to 9 times daily, typically 4 times daily. For less advanced cases of neurofibromatosis, oral treatment is effective. Typically, the patient is given the combination, such as Antineoplaston AS2-1 capsules, from 1 to 20 g/day, or 20 mg/kg/24 h to 300 mg/kg/24 h, and preferably, 10 g/day or 150 mg/kg/24 h. For advanced cases of neurofibromatosis, treatment in the form of intravenous or intraarterial infusions or injections can be used. The injections can be administered as frequently as 48 times a day, through intravenous catheter and computerized infusion pump. The dosages for the combination of sodium salt phenylacetylglutamine and sodium salt of phenylacetic acid are from 0.02 to 1.15 g/kg/24 hr.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, capsules, elixirs, suspensions, syrups or the like. Pharmaceutically compatible binding agents and/or adjuvant materials can be included as part of the composition.

Although not required, the combination of active ingredients may be provided in a composition that protects it from the acidic environment of the stomach. The composition can be orally administered in combination with an antacid formulation. The composition can also be administered in an enteric coating that maintains its integrity in the stomach and releases the active compounds in the intestine.

The active compounds can also be mixed with other active materials that do not impair the desired action, or with materials that supplement the desired action, including immunosuppressive or anti-inflammatory agents.

Solutions or suspensions used for parenteral, intradermal, or subcutaneous application can include the following components: a sterile diluent such as water for injection, normal saline solution, phosphate buffered saline, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, titrates or phosphates and agents for the adjustment of tonicity such as sodium chloride or dextrose. The parenternal preparation can be enclosed in ampoules, disposable syringes or multiple dose vials made of glass or plastic, or plastic infusion bags.

The following examples illustrate the treatment with AS2-1 of two patients suffering from neurofibromatosis Type1 and 2.

EXAMPLE 1

Patient L.A.

When coming under my care, the patient was a 14 year old white female who was complaining of occasional headaches, nausea, right facial nerve paresis, slightly decreased vision, and difficulty expressing herself, presence of café-au-lait spots on the skin and a nodule in the right breast area.

At the age of 5, the patient developed paralysis of the sixth cranial nerve. At the age of 7, she had a CT scan of the brain which was negative. At that time, she underwent two corrective surgeries for the sixth nerve paralysis. In 1992, the patient developed slowly progressing facial nerve paresis. The MRI of the brain on Jul. 18, 1992 showed nodule of the left internal auditory canal and focal enhancing nodule on the left side of the entrance to the Meckel's cavum. There was also an area of enhancement anterior to the pons with involvement of the left mammillary body and enhancement of the tip of the internal auditory canal on the right side. The patient was diagnosed as having neurofibromatosis Type 2.

The treatment with AS2-1, 500 mg capsules began on Dec. 2, 1992. Initially, the patient was taking 2.5g of the formulation four times a day (0.15 g/kg/day). On Jun. 27, 1993, the dose was increased to 2.5 g seven times a day (0.26 g/kg/day). The patient continues the treatment at such dosage level at present. She tolerates the treatment well without any significant side effects. The initial evaluation of the response to the treatment after six weeks of the therapy has shown slight decrease of the size of the spots on the skin of the back. The patient was not complaining anymore of headaches, nausea, and decreased vision. The follow-up examination after five months of treatment revealed decrease of the nodule on the skin of the fight breast and disappearance of discoloration of the nodule. This nodule continued to decrease as confirmed by physical examination done after seven months of treatment.

A complete evaluation of the patient's condition after eleven months of treatment has shown further decrease of the size of the nodule in the fight breast. The MRI done at the end of October 1993 has shown decrease of the number of nodules in the brain and decrease in the size of the nodule in the left auditory canal. The patient had marked symptomatic improvement. She did not complain of headaches, nausea, or decreased vision anymore. She did not have difficulty expressing herself. Her facial nerve paresis also improved.

EXAMPLE 2

Patient A.S.

The patient is a 7 year old white male who at the age of 4 developed multiple nodules and café-au-lait spots on the skin, and was diagnosed with neurofibromatosis Type 1. The MRI of the brain on Sep. 8, 1993 revealed a nodule in the area of the crossing of optic nerves. The patient began the treatment with AS2-1 capsules on Oct. 1, 1993 and is taking 1.5 g po three times a day (0.15 g/kg/day). The initial evaluation after the first six weeks of treatment has shown decrease of the size of the nodules. The patient had further improvement after six months of treatment. The nodules on the lower extremities and the back completely disappeared. His mental status and behavior improved significantly as confirmed by psychological tests.

What is claimed is:

1. A method of treating neurofibromatosis in an afflicted human host comprising:
    administering to the host a pharmaceutical composition containing a therapeutically effective amount of a combination of compounds of the formula:

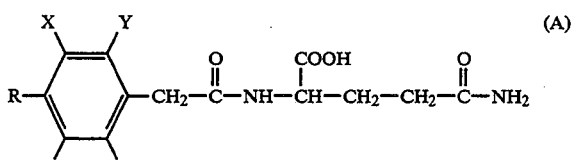

and

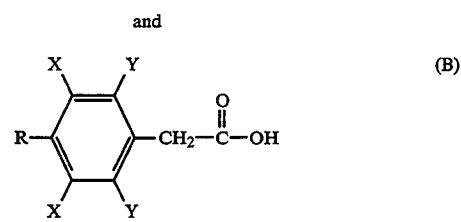

in a weight ratio ranging from about 1:1 to about 1:10 (A:B);
    wherein R is OH, $NH_2$, OW, or H;
    X is H, F, Cl, Br, I, OH, OW, $NO_2$ or $NH_2$;
    Y is H, F, Cl, Br, or I;
    W is

or a $C_1$ to $C_{12}$ aliphatic group;
    Z is an aliphatic or aromatic group of $C_1$ to $C_{12}$;
    X and Y can both vary within the compound; or pharmaceutically acceptable salts thereof.

2. The method of claim 1 wherein the pharmaceutical composition contains a mixture of phenylacetylglutamine and phenylacetic acid or pharmaceutically acceptable salts thereof.

3. The method of claim 1 wherein the pharmaceutical composition contains a 1:4 ratio of A:B.

4. The method of claim 2 wherein the pharmaceutical composition contains a 1:4 ratio of phenylacetylglutamine sodium salt and phenylacetic acid sodium salt.

5. The method of claim 1 wherein the pharmaceutical composition is administered to humans in the amount of 1.0 to 20 g/day.

6. The method of claim 1 wherein the pharmaceutical composition is administered orally or parenterally.

* * * * *